United States Patent [19]

Lagerman

[11] Patent Number: 5,182,033

[45] Date of Patent: Jan. 26, 1993

[54] POLYAMIDE SALTS

[75] Inventor: Robert K. Lagerman, Dublin, Ohio

[73] Assignee: Sherex Chemical Company, Inc., Dublin, Ohio

[21] Appl. No.: 715,381

[22] Filed: Jun. 14, 1991

[51] Int. Cl.$^5$ .......................................... D06M 10/08
[52] U.S. Cl. .................................... 252/8.6; 252/8.7; 252/8.75; 252/8.8; 252/8.9; 548/349.1; 554/58
[58] Field of Search .................... 252/8.6, 8.7, 8.75, 252/8.8, 8.9, 547; 548/341, 342, 337; 260/462 R

[56] References Cited

U.S. PATENT DOCUMENTS

| | | | |
|---|---|---|---|
| 3,095,373 | 6/1963 | Blomfield | 252/8.8 |
| 3,167,554 | 1/1965 | Ernst | 260/268 |
| 3,424,771 | 1/1969 | Libby | 260/404.5 |
| 3,436,463 | 4/1969 | Mayhew et al. | 424/320 |
| 3,442,692 | 8/1965 | Gaiser | 252/8.8 |
| 3,634,947 | 1/1972 | Furgal | 117/109 |
| 3,676,199 | 10/1970 | Hewitt et al. | 252/8.8 |
| 3,686,025 | 8/1972 | Morton | 117/140 |
| 3,980,643 | 9/1976 | Kato et al. | 260/268 |
| 4,068,069 | 1/1978 | Kato et al. | 542/427 |
| 4,127,489 | 11/1978 | Pracht et al. | 252/8.8 |
| 4,237,016 | 12/1980 | Rudkin et al. | 252/8.8 |
| 4,339,391 | 7/1982 | Hoffmann et al. | 260/401 |
| 4,370,272 | 1/1983 | Wechsler et al. | 252/8.8 |
| 4,399,044 | 8/1983 | Richmond | 252/8.8 |
| 4,459,400 | 7/1984 | Kuhfuss et al. | 528/289 |
| 4,486,195 | 12/1984 | Weinstein et al. | 252/8.8 |
| 4,555,349 | 11/1985 | Butterworth et al. | 252/8.6 |
| 4,589,988 | 5/1986 | Rieck et al. | 252/8.8 |
| 4,724,089 | 2/1988 | König et al. | 252/8.8 |
| 4,767,547 | 8/1988 | Straathof et al. | 252/8.8 |
| 4,889,643 | 12/1989 | Royce et al. | 252/547 |
| 4,906,394 | 3/1990 | Gutierrez et al. | 252/81.5 A |
| 4,975,091 | 12/1990 | Becker et al. | 252/8.8 |
| 4,976,878 | 12/1990 | Coffindaffer | 252/8.8 |
| 4,994,193 | 2/1991 | Wahl | 252/8.8 |

FOREIGN PATENT DOCUMENTS 0040562 11/1981 European Pat. Off. .
0239910 10/1987 European Pat. Off. .
1593921 7/1970 France .
1071298 8/1964 United Kingdom .

OTHER PUBLICATIONS

Lesieur Cotelle et Associes S.A. Chem. Abst. 96-8527e (1982).
Hotoda et al. Chem. Abst. 105-226649s (1986).
Straathof et al Chem. Abst. 108-53382r (1988).

Primary Examiner—A. Lionel Clingman
Assistant Examiner—William S. Parks
Attorney, Agent, or Firm—Scully, Scott, Murphy & Presser

[57] ABSTRACT

Disclosed are compounds useful as biodegradable fabric softeners, of the general formula:

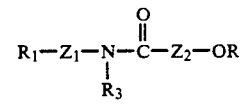

wherein
R is alkyl containing up to 22 carbon atoms, alkyl containing up to 22 carbon atoms and one or more ethylenic bonds, acyl containing 2 to 22 carbon atoms, or H;
$R_1$ is

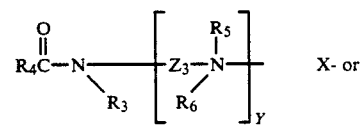

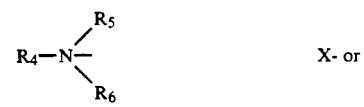

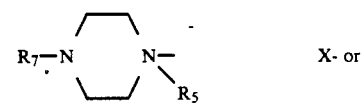

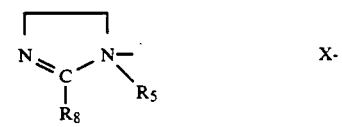

$Z_1$, $Z_2$, and $Z_3$ are each alkylene containing 2-8 carbon atoms in the principal chain and a total of up to 15 carbon atoms;
Y is an integer from 1-3;
$R_3$ is methyl, ethyl or H;
$R_4$ and $R_5$ are each alkyl containing up to 22 carbon atoms, alkyl containing up to 22 carbon atoms and one or more ethylenic bond, or —$Z_2$—OR;
$R_5$ is methyl, ethyl, hydroxymethyl, hydroxyethyl, or H;
$R_6$ is methyl, ethyl, hydroxymethyl, hydroxyethyl, or benzyl;
$R_7$ is

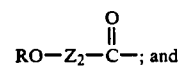

X—is a salt forming anion.

24 Claims, No Drawings

POLYAMIDE SALTS

The present invention relates to biodegradable compounds which exhibit hydrolytic stability upon storage. These compounds are amides of polyamines which include ester groups. They are useful as fabric softener compositions with antistatic properties, as hair conditioners, as clay modifiers and as sugar decolorizers.

BACKGROUND OF THE INVENTION

Fabric conditioning for improved softening and antistatic properties is normally achieved by any of the general methods including, for example, the addition of a fabric softening agent to the rinse cycle of a normal wash routine; the use of a substrate impregnated with a fabric conditioner composition for use in the dryer where the fabric conditioning agent is transferred to the clothes in the dryer; and the inclusion of the fabric softening agent with a detergent formulation for the wash cycle.

Commercial fabric conditioner formulations are most commonly based on quaternary ammonium salts. Formulations for use in the final clear water rinse, and dryer and detergent softeners, are normally based on difatty dimethyl quaternary salts, for example, dihydrogenated tallow dimethyl ammonium chloride (Adogen 442, Sherex Chemical Co., Inc.) or diamidoamine quaternary (Varisoft 222 Sherex Chemical Co., Inc.) or imidazoline based quaternaries.

Within recent years, there has developed a need for fabric softening compositions with faster biodegradation. Quaternary compounds with long chain alkenyl groups interrupted by ester groups are known, from e.g., French Patent 1,593,921. Softening compositions containing such materials are disclosed in European Patent No. 0 040 562.

U.S. Pat. No. 4,767,547 claims to attain rapid biodegradation by the inclusion of ester groups in long chain substituents of quaternary ammonium compounds. Similarly, U.S. Pat. No. 4,339,391 discloses esters based on hydroxyalkyl ammonium quaternary salts. U.S. Pat. No. 3,167,554 describes the reaction of a piperazine with polybasic acids to form polyamides with specific reference to the reaction between polybasic acids and hydroxyethyl piperazine wherein the amide formation is carried out under conditions which inhibit esterification of the hydroxy group.

U.S. Pat. No. 4,068,069 and 3,980,643 disclosed the preparation of esters of hydroxyalkylpiperazine using conditions which result in esterification with no amide formation.

There are numerous references to the reaction of lactones with amines leading to the corresponding hydroxyamides. U.S. Pat. No. 4,906,394 discloses many references having to do with the reaction between lactones and polyamines, and specifically discloses reaction of a monoamide of a polyamine with butyrolactone. U.S. Pat. No. 4,589,988 discloses and claims imidazoline structures having groups obtainable via lactone condensations. U.S. Pat. No. 3, 436,463 discloses the procedures and products obtained from the reaction of lactones with diamines, triamines, hydroxyalkyldiamines, and morpholine. U.S. Pat. No. 3,424,771 discloses the reaction of the mono fatty acid amide of ethylene diamine with lactones to form the hydroxy amide.

SUMMARY OF THE INVENTION

The present invention provides compositions containing the new quaternary ammonium salts which rapidly biodegrade but are sufficiently shelf stable for commercial utility. The invention further provides the new quaternary salts which have satisfactory softening properties for rinse cycle, dryer cycle or wash cycle use while displaying acceptable biodegradation coupled with sufficient shelf stability.

DETAILED DESCRIPTION OF THE INVENTION

This invention relates to compounds of the formula:

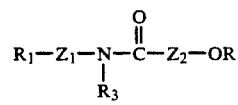

wherein:
R is alkyl, alkyl containing one or more ethylenic bonds, acyl or H;
$R_1$ is

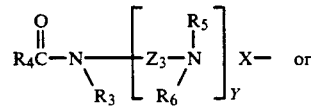

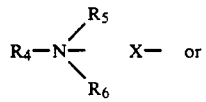

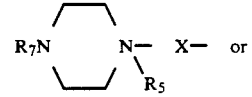

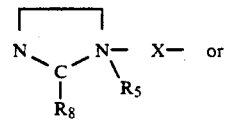

$Z_1$, $Z_2$ and $Z_3$ are each alkylene containing 2–8 carbon atoms in the principal chain and a total of up to 15 carbon atoms;
Y is an integer from 1–3;
$R_3$ is lower alkyl or H;
$R_4$ and $R_8$ are each alkyl, alkyl containing one or more ethylenic bonds, or —$Z_2$—OR;
$R_5$ is lower alkyl, lower hydroxyalkyl or H;
$R_6$ is lower alkyl, hydroxy lower alkyl lower alkenyl or benzyl;
$R_7$ is acyl or

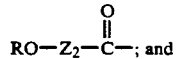

X— is a salt forming anion.

The acyl groups descriptive of R and $R_7$ are derived from aliphatic acids, preferably fatty acids, natural or synthetic, containing from 2 to about 22 carbon atoms. The naturally-occurring fatty acids are derived from fats and oils as is well-known in this art and include stearic, linoleic, isostearic, oleic, lauric, myristic, and others, and usually include a mixture of related homologous acids. Tallow acids, for example, are mainly $C_{16}$–$C_{18}$, and include ethylenic unsaturated. Hardened tallow acids are produced by hydrogenation of tallow acids. Tall oil fatty acids also comprise a mixture of $C_{16}$–$C_{22}$ acids which are primarily oleic and linoleic acids. Other acids derived from natural sources include coconut oil acids, mainly $C_{12}$–$C_{18}$ fatty acids with some unsaturation.

The alkyl groups and alkyl containing one or more ethylenic, i.e. double bonds, representative of R, $R_4$ and $R_8$ contain up to 22 carbon atoms and are preferably derived from naturally-occurring acids such as are already described hereinbefore by methods well known in the art.

The salt-forming anion representative of X can be organic or inorganic anions commonly employed in the formation of quaternary or acid addition salts of tertiary amines and include, for example, halide ($Cl^-$, $Br^-$, $I^-$), alkyl sulfate, e.g., methyl sulfate, carbonate or alkyl carbonate, e.g., tartrate, acetate, stearate and like. Preferred anions are chloride, methyl, sulfate and methylcarbonate.

Preferred compounds of this invention are enumerated in Table I.

TABLE I

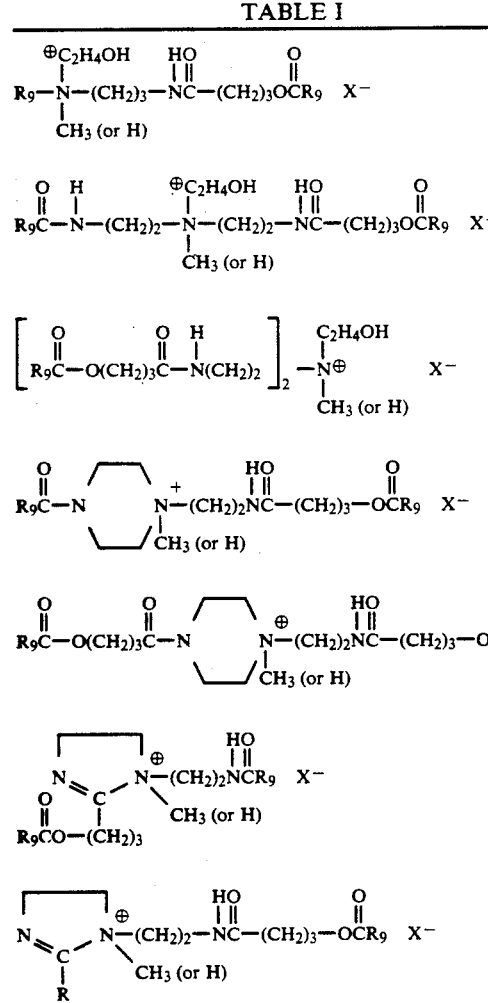

TABLE I-continued

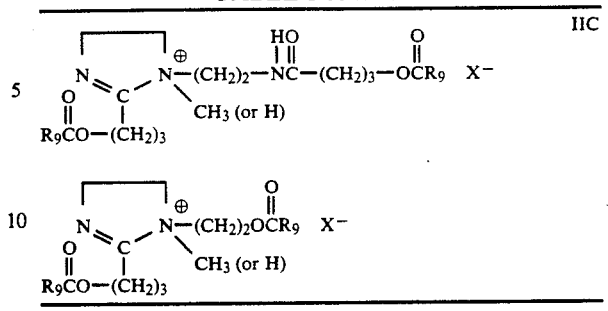

In the preferred compounds of Table I, $R_9$ is a saturated or unsaturated aliphatic radical containing 12–18 carbon atoms in straight or branched chains. In these compounds, $R_9$ is preferably derived from naturally-occurring sources such as tallow, vegetable oils, fish oils and the like. $R_9$ is most preferably derived from hydrogenated tallow acids for softening and from coconut oil or synthetic sources for personal care including hair treatment. Thus, in the following preferred compounds $R_9$ is the aliphatic radical obtained from tallow acids, hydrogenated tallow acids, and coconut oil acids. Accordingly, $R_9$ may comprise a mixture of aliphatic groups containing 12–18 carbon atoms as is the general case in this art.

The most preferred compounds are those wherein $R_9$ is a mixture of $C_{15}$–$C_{17}$ alkyls derived from hydrogenated tallow acids or $C_{13}$–$C_{15}$ derived from coconut fatty acids.

The compounds of this invention can be readily produced by known reactions. Most preferred reactions involve the use of lactones, which are cyclic esters, that easily react with polyamines. After formation of the amides, the salts thereof are formed by reaction with suitable reagents.

Useful amine compounds for reaction with the lactones include polyamines having from 2 to 60 total carbon atoms in the polyamine reactant, preferably between 2 and 26 total carbon atoms, and most preferably 18 to 25 carbon atoms. These amines may be hydrocarbyl amines or may be hydrocarbyl amines including other non-interfering groups such as alkoxy groups, amide groups, nitro groups, piperazine, imidazoline groups and the like.

Preferred examples of suitable amine compounds include ethylene diamine; 1,3-propylene diamine; 1,6-diaminohexane; diethylenetriamine, triethylene tetramine, polyalkoxydiamines; and n-octadecyl 1,3-propylene diamine; N-aminoethylpiperazine; dipropylene triamine; N-aminoethylimidazoline; monoamides of polyamines.

The usual process for the production of the compounds of this invention involves reaction of suitable polyamines with lactones. Useful lactone compounds for forming the intermediate hydroxy amides for conversion to the products of this invention have from 3–9 carbon atoms in the lactone ring. The lactone may be substituted or unsubstituted, and the substituents, if any, may comprise, for example, alkyl, aryl, aralkyl, cycloalkyl, alkoxy or other groups which will not interfere with the ring opening reaction and amide formation. The preferred lactones have no more than 2 substituent groups, and the more preferred lactones are unsubstituted. Preferred examples of useful lactones include delta valerolactone gamma butyrolactone, methyl delta valerolactone, epsilon-caprolactone, methoxy-epsilon-caprolactone, and the like, with butyrolactone and epsilon-caprolactone being particularly preferred.

Reaction of the Lactone With a Polyamine

The lactones react with the polyamines under relatively mild conditions to yield hydroxy terminated amides which contain methylene units between the hydroxy group and the amide. Although the reaction of the lactone with the amines can lead to polymerization, the most desirable products for this invention involve a single adduct reaction. The hydroxy group generated by the condensation of the lactone with the amine can be esterfied with carboxylic acids using standard reaction conditions.

The preparation of compound IA from Table I is shown in the following Sequence I.

3300 cm$^{-1}$ (OH or NH stretch); 1650 cm$^{-1}$ (C = O, amide), no carbonyl stretch due to lactone. The thin layer chromatograph of this material is consistent with a single component. $^{13}$C NMR confirms the presence of the following groups: Δ173.59 (amide carbonyl), 62.00 (CH$_2$—OH), 50.00 (R—CH$_2$—NH; R = tallow linkage,

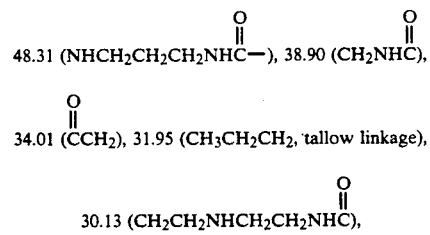

SEQUENCE I

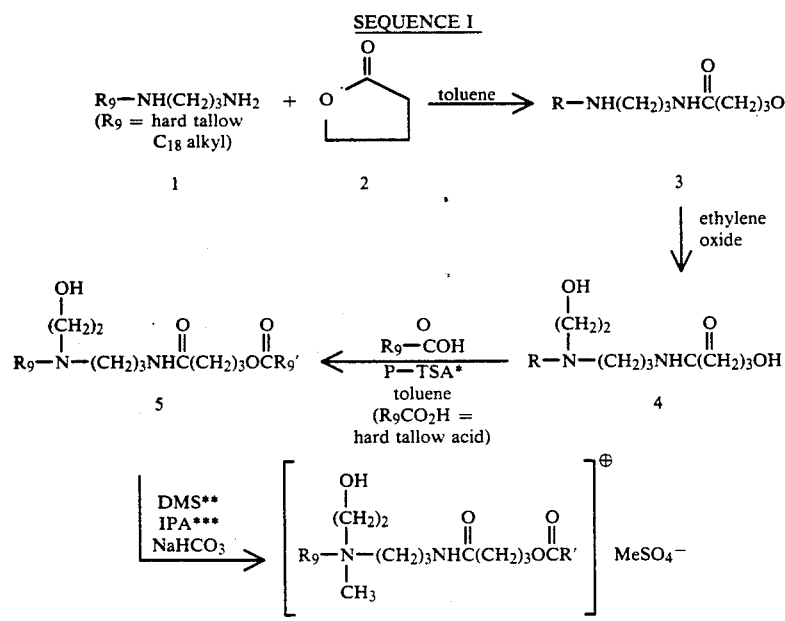

* para-toluenesulfonic acid
** dimethylsulfate
*** isopropanol

The following examples are provided to further illustrate the invention.

EXAMPLE 1

Procedure For Synthesis of Lactone Adduct 3 of Sequence 1

Into a 2-L 4-neck flask is placed 400 g (1.23 mole) of hard tallow amino propylamine (1) (Adogen 540D, Sherex Chemical Company) 105.78 g (1.23 mole) of butyrolactone (2) (Aldrich), and 500 ml of toluene. The flask is fitted with a mechanical stirrer, reflux condenser, and thermometer. The reaction mixture is heated to reflux and the reaction monitored by TAV (ASTM method 02073-66, total amine value). When the TAV remains constant, the reaction is stopped and the toluene removed in vacuo. The resulting solid is recrystallized from ethyl acetate to produce 377 g (74.5%) of a white solid. The TAV = 137, 2-3 AV = 132, and 3 AV = 3. The theoretical TAV and 2-3 AV = 138 IR spectra (Perkin-Elmer 1420 Ratio Recording Infrared Spectrophotometer) is consistent with the structure;

29.38-29.73 (CH$_2$ middle portion of fat group),

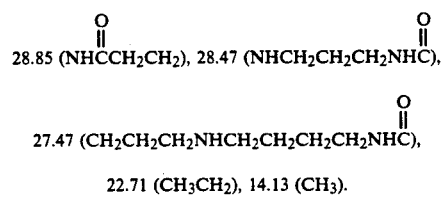

22.71 (CH$_3$CH$_2$), 14.13 (CH$_3$).

Ethoxylation of Lactone Adduct (4)

To a clean, dry 2-L Parr reactor is placed 356 g (0.87 moles) of Compound 3. The reactor is purged with nitrogen and then pressured to 10 psi with nitrogen. The amine 3 is heated to 150° C. and ethylene oxide (40.0 g, 0.90 mole) added over a period of fifteen minutes, causing a strong exotherm to occur. After addition is complete the reaction mixture is maintained at 150° C. and 50–60 psi for 2 hours. The reactor is cooled to 110° C.

and any excess ethylene oxide is stripped off. The reaction produces 351.9 g (97.7% yield).

| Actual TAV = 135 | Theor. TAV = 124 |
|---|---|
| 2-3 AV = 131 | 2-3 AV = 124 |
| 3 AV = 131 | 3 AV = 124 |

TLC analysis: (90:15:2:1; $CHCl_3$: MeOH: $HCO_2H$: $H_2O$ $R_f$ = 0.16 consistent with single component.

IR analysis: 3300 $cm^{-1}$ (OH or NH stretch), 1640 $cm^{-1}$ (C = O amide).

CNMR analysis confirms the presence of the following groups.

173.79 (H—N—$\overset{O}{\overset{\|}{C}}$), 61.77 ($CH_2OH$, lactone fragment), 59.74 N—$CH_2$, EO fragment), 59.30 ($CH_2$—OH, EO fragment), 55.99 ($CH_2$—N, tallow fragment), 52.64 (N—$CH_2\underline{CH_2}CH_2NH\overset{O}{\overset{\|}{C}}$), 39.67 ($\underline{CH_2}NH\overset{O}{\overset{\|}{C}}$), 33.54 ($\underline{CH_2}\overset{O}{\overset{\|}{C}}$), 31.94 ($CH_3CH_2\underline{CH_2}$), 29.97 ($\overset{O}{\overset{\|}{C}}CH_2\underline{CH_2}$), 29.71–26.63 (tallow methylenes), 22.67 ($CH_3\underline{CH_2}$), 14.10 ($CH_3$).

Procedure For Synthesis of Ester of the Ethoxylated Amide (5)

In a 1-L 3-neck flask fitted with a stir bar, water trap, thermometer, and reflux condenser is placed 351.95 g (0.85 mole) of the ethoxylated amide (4) 241.4 g (0.85 mole) of stearic acid (Hydrofol 1895, Sherex Chemical Co.) 1.62 g (0.085 mole) of p-toluene sulfonic acid monohydrate, and 50 ml of toluene. The mixture is heated to 174–180° C. while stirring and the reaction monitored by Acid Value (AV) and the volume of water collected in the trap. After 28 hours, the Acid Value is 2 and there are 15.5 ml of water in the trap (Theor. AV = O, ml $H_2O$ =O 15.3). The reaction mixture is then cooled to 100° C., poured into a 1-L round bottom flask and the toluene removed on a rotovap. The yield is 573.19 g (99%).

|  | Actual TAV = 74 | Theor. TAV = 82 |
|---|---|---|
| secondary tertiary amine value | 2-3 AV = 74 | 2-3 AV = 82 |
|  | 3 AV = 74 | 3 AV = 82 |
| tertiary amine | AV = 2.4 | AV = 0 |

The lower amine values probably results from formation of a small amount of diester which would increase the molecular weight. IR analysis is consistent with the proper structure (3300 $cm^{-1}$, OH stretch; 1770 $cm^{-1}$, 1730 cm–1 C = O, ester, C = O ester; 1650 $cm^{-1}$, C = O amide). TLC analysis shows a spot with an $R_f$ different than the starting material. $R_f$ ester = 0.4; $R_f$ ethoxylate = 0.16; 90:15:2:1, $CHCl_3$: MeOH: HCOOH: $H_2O$.

$^{13}$CNMR analysis:

δ 173.8 ($\overset{O}{\overset{\|}{C}}$NH), 173.3 ($\overset{O}{\overset{\|}{C}}$O), 59.00 ($CH_2$—N, EO adduct)

55.86 ($CH_2OH$), 54.19 ($CH_2NCH_2$), 52.08 ($CH_2NCH_2$).

36.87 ($\underline{CH_2}NH\overset{O}{\overset{\|}{C}}$), 34.34 (NH$\overset{O}{\overset{\|}{C}}\underline{CH_2}$), 31.95 ($\underline{CH_2}\overset{O}{\overset{\|}{C}}$O), 30.01 ($CH_2CH_2CH_3$), 29.71–24.98 (tallow and stearyl methylenes), 22.70 ($CH_3CH_2$), 14.10 ($CH_3$). The core structure indicates that an ester is formed.

Synthesis of Dimethyl Sulfate Quaternary Salt of Ester Amide Alcohol (6)

In a 250 ml 3-neck flask fitted with a stir bar, thermometer, reflux condenser, and addition funnel is placed 45 g (0.058 mole) of the ester amide alcohol (5), 60 ml of IPA, and 4.87 g (0.058 mole) of $NaHCO_3$. Stirring is commenced and the reaction mixture heated to 60° C. At this time dimethyl sulfate (DMS) (7.32 g, 0.058 mole) is added dropwise via the addition funnel resulting in an exotherm. After addition is complete, the temperature is maintained at reflux (78° C.) and the mixture allowed to stir for 2 hours. The TAV is 5.3 and the AV is 1.16. An additional 1.5 g of DMS is added at this point and the mixture allowed to stir for an additional hour. The TAV is 1.3 and the AV is 0.85. The reaction is stopped at this point and the mixture filtered under vacuum, followed by removal of the solvent from the filtrate in vacuo to yield 48.04 g (92% yield) of a yellowish solid.

| Actual TAV = 2.76 | Theor. TAV = 0 |
|---|---|
| Actual AV = 1.06 | Theor. AV = 0 |

IR Analysis: 3300 $cm^{-1}$ (OH NH stretch), 1770 $cm^{-1}$ (C = O, ester) 1730 cm–(C = O, ester), 1650 $cm^{-1}$ (C = O, amide).

TLC analysis 90:15:2:1 $CHCl_3$: MeOH: HCOOH: $H_2O$ $R_f$ ester = 0.4
$R_f$ quat = 0.28

$^{13}$CNMR analysis shows that this material is indeed a mono methyl quat ( 54.55, $CH_3SO_4$; 49.27, NMe).

EXAMPLE 2

Preparation of Compound Ib - IIc

The compounds of Table I are prepared by the following procedures.

Preparation of Ib

The preparation of Ib is effected by reaction of equimolar amounts of diethylenetriamine (DETA) and butyrolactone at room temperature and the resulting product is reacted with equimolar amounts of a carboxylic acid or its methyl ester to produce the monoamide. The resulting amide is reacted with 1 mole of ethylene oxide (EO) The amine is then esterified with a equimolar amount of a fatty acid or methyl ester and the resulting product is quaternized with an appropriate quaternizing agent under standard conditions (methyl chloride, methyl bromide, dimethyl sulfate, etc.) or neutralized with acid.

Preparation of Ic

The preparation of Ic is accomplished by reacting two moles of butyrolactone with 1 mole of DETA at room temperature. The resulting adduct is ethoxylated with 1 mole of EO, esterified with the appropriate carboxylic acid or its methyl ester, and either quaternized or neutralized as in the preparation of Ib.

Preparation of Id

The preparation of Id is accomplished by reacting equimolar amounts of butyrolactone and amino ethyl piperazine (AEP) at room temperature. The resulting product is reacted with two moles of a carboxylic acid or methyl ester to produce the corresponding ester amide which is next quaternized or neutralized with acid.

Preparation of Ie

The preparation of Ie is accomplished by heating 2 moles of butyrolactone with 1 mole of AEP. The resulting product is reacted with 2 moles of a carboxylic acid or its methyl ester under standard esterification conditions and finally is quaternized or neutralized with acid.

Preparation of IIa

The preparation of IIa is effected by reacting 1 mole of butyrolactone with 1 mole of DETA at room temperature followed by heating at 150° C. and 0.2 mm pressure to cyclize to the imidazoline (JACS, 60(4), 1983, 823-838). The resulting product is then reacted with 2 moles of a carboxylic acid or its methyl ester using a standard catalyst to form the ester amide of the imidazoline. This ester amide is finally quaternized or neutralized with acid.

Preparation of IIb

The preparation of IIB is accomplished by reacting 1 mole of a carboxylic acid with 1 mole of DETA under standard amidation reaction conditions followed by cyclization to the imidazoline under similar reaction conditions for preparing IIa. The resulting product is then reacted with 1 mole of butyrolactone at room temperature. The resulting product is next esterified using standard esterification conditions producing a product which is next quaternized or neutralized with acid.

Preparation of IIc

The preparation of IIc is accomplished by reacting two moles of butyrolactone with 1 mole of DETA at room temperature followed by cyclization to the imidazoline under similar conditions for preparing IIa. The resulting product is esterified under standard conditions to produce a product which is quaternized or neutralized.

The anion $X^-$ represents any salt-forming anion, including but not limited to $Cl^-$, $Br^-$, $F^-$, $MeSO_4^-$, $CO_3^-$, organic acid anion (e.g., acetate, lactate, stearate) inorganic acid anion (e.g., phosphate). Most preferred for use in textile softening are the halides, methylsulfate and carbonate salts or quaternaries.

EXAMPLE 3

Softening Evaluation

The softening characteristics of the compounds of this invention were evaluated using standard testing procedures established by the CSMA (Chemical Specialties Manufacturers Association). These tests include DCC-13-E for fabric stripping; D-13-A for fabric treatment procedure; D-13-B for softener evaluation by test panel scoring, and D-13-B for measurement of static control. Towels were evaluated by human subjects for softness rankings. Panel members are forced to rank the towels in order of their preference, therefore the result is a ranking, and not a rating.

Measurement of static is done as the dried towels are removed from electric clothes dryers. Static reduction is determined by comparing treated towels to untreated towels (harsh control). The Simco electrostatic Locator is used for this measurement as described in CSMA Method D-13F.

The compounds which were evaluated for softening are shown in Table II.

TABLE II

X
$$R-\overset{\overset{CH_3}{|}}{\underset{\underset{R}{|}}{N}}-CH_3^{\oplus}\quad X^-$$

R = hydrogenated tallow alkyl ($C_{16}$–$C_{18}$)
X = Cl

XI
$$\begin{array}{c}R-\overset{O}{\overset{\|}{C}}-NH-CH_2CH_2\\ R-\overset{O}{\overset{\|}{C}}-NH-CH_2CH_2\end{array}\diagup N\diagdown \begin{array}{c}CH_3^{\oplus}\\ R^1\end{array}\quad X^-$$

$R-\overset{\|}{\underset{O}{C}}$ = tallow acids
$R^1$ = hydroxyethyl
X = methyl sulfate XII
$$R-C\diagup\underset{\underset{CH_3}{\diagup}\overset{\oplus}{\underset{|}{N}}-CH_2}{\overset{N-CH_2}{\diagdown}}\overset{\oplus}{X^-}$$
$$CH_3\quad CH_2CH_2N\overset{\|}{\underset{O}{C}}R$$

R = tallow alkyl ($C_{15}$–$C_{17}$)
X = methyl sulfate

XIII
$$R-\overset{O}{\overset{\|}{C}}-O(CH_2)_2\overset{\overset{CH_3}{|}}{\underset{\underset{CH_3}{|}}{N}}-R^1\overset{\oplus}{\quad}\quad X^-$$

R = $C_{15}$ alkyl
$R^1$ = $C_{16}$ alkyl
X = Cl

Ia
$$R-\overset{\overset{(CH_2)_2}{\diagup}}{\underset{\underset{CH_3}{|}}{N}}\diagdown(CH_2)_3NH\overset{O}{\overset{\|}{C}}(CH_2)_3O\overset{O}{\overset{\|}{C}}R^1\overset{\oplus}{\quad}\quad X^-$$

R = hydrogenated tallow alkyl ($C_{16}$–$C_{18}$)
$R^1$ = $C_{17}$ alkyl
X = methyl sulfate

| Preparation of Softener Formulations | |
|---|---|
| Ingredients | Weight in Grams |
| softener solids | 8.92 |

-continued

| Preparation of Softener Formulations | |
|---|---|
| Ingredients | Weight in Grams |
| calcium chloride | sufficient to control viscosity; less than 1.0% |
| water-150 ppm hardness | sufficient to make 200 gram total |

1. Heat 150 ppm water as needed to disperse the softener.
2. Heat the surfactant candidate until completely fluid.
3. Agitate the water at approximately 500 rpm using high shear mixer. Continue mixing throughout the preparation.
4. Slowly add the fluid softener candidate in small portions, alternating with the calcium chloride. The addition of the calcium chloride is on an as needed basis to control viscosity.
5. Increase agitation rpm as needed to attain dispersion of the softener candidate.
6. Agitate the dispersion until it cools to room temperature.
7. Add any additional room temperature 150 ppm water to attain final weight of 200 grams.
8. Agitate for 10-15 minutes.

Results of Softening Evaluation on 100% Cotton Hand Towels

| Test I Softening Rank (4 = Best) | | | |
|---|---|---|---|
| Structure Tested | Panel 1 | Panel 2 | Average |
| X | 3.3 | 3.4 | 3.4 |
| XIII | 2.9 | 2.9 | 2.9 |
| Ia | 2.6 | 2.8 | 2.7 |
| Untreated Control | 1.3 | 1.0 | 1.2 |

Use level = 0.1% based on the dry weight of the fabric bundle

| Test II Softening Rank (5 = Best) | | | |
|---|---|---|---|
| Structure Tested | Panel 1 | Panel 2 | Average |
| X | 4.63 | 4.50 | 4.6 |
| Ia | 3.13 | 3.88 | 3.5 |
| XII | 3.25 | 3.38 | 3.3 |
| XI | 3.00 | 2.25 | 2.6 |
| Untreated Control | 1.00 | 1.00 | 1.0 |

Use level = 0.1% based on the dry weight of the fabric bundle

Results of Static Testing

| Test III Static Reduction Data | | | |
|---|---|---|---|
| Structure Tested | % RH | Voltage | % Static Reduction |
| Untreated control | 33 | 7905 | — |
| Ia | 32 | 3215 | 59.3 |
| X | 33 | 3710 | 53.1 |
| XIII | 33 | 3600 | 54.5 |

Use level = 0.1% based on the dry weight of the fabric bundle

| Test IV | | | |
|---|---|---|---|
| Structure Tested | % RH | Voltage | % Static Reduction |
| Untreated control | 30 | 5510 | — |
| Ia | 32 | 1885 | 65.8 |
| X | 30 | 3310 | 43.6 |
| XII | 30 | 187 | 94.8 |

Use level = 0.1% based on the dry weight of the fabric bundle

Biodegradation

It is becoming increasingly important that fabric softening compositions have improved rate of biodegradation. The preferred compound of this invention (structure Ia) was evaluated for rate of biodegradation according to the following procedure (Modified Closed Bottle Test). The following describes a method, the modified closed bottle test (MCBT), which can be used to determine the relative biodegradability of surfactants and which overcomes some of the problems of other methods when used to measure the biodegradability of quaternary ammonium compounds (QAC).

Evaluations of the biodegradability of QAC are more complicated than those of anionic or nonionic surfactants for the following reasons: (1) QAC's are readily adsorbed on surfaces, even more than other classes of surfactants. (2) Many QAC surfactants have bactericidal abilities above 50 ppm. Evaluations conducted with cationic detergents above this concentration have often been inaccurate since the bacteria were killed leading to the conclusion that the materials were not biodegradable. (3) Bacteria used in a laboratory setting are often not readily able to use QAC's as a food source. Similar bacteria found in natural waters, or in publicly operated treated works (POTW), are able to degrade QAC's. This is due to naturally occurring bacteria being acclimated to QAC's because of their regular exposure to the surfactants in lakes, rivers, etc. Extra care is needed to ensure lab testing closely models realistic environmental conditions.

Materials and Equipment

The QAC's evaluated were di(hydrogenated tallow) dimethylammonium chloride (Adogen 442 (Compound X)); lauryltrimethylammonium chloride (Compound XVI); distearlyldimethylammonium chloride (Arosurf TA (Compound XV); methyl,1-tallowamidoethyl, 2-tallowimidazolinium methyl sulfate (Varisoft 222 (Compound XI)). All compounds were obtained from Sherex Chemical Co. (Dublin, Ohio). The compounds with trade names in parentheses were used as supplied. The others were purified and recrystallized from appropriate solvents. The bacteria were obtained as Polyseed (tm) (Baxter); Polyseed is a mixture of 12 bacteria which are characteristic of those found in wastewater and POTW. HPLC grade water was used (Fisher) and dissolved oxygen was measured with a dissolved oxygen probe and dissolved oxygen was measured with a dissolved oxygen probe and meter (Yellow Springs Instruments, Model 58). Biodegradation samples were incubated at 20° +/− 0.3 ° C. in the dark.

Acclimation of Bacteria

A pellet of Polyseed was dispersed into 250 ml dilution water where the oxygen level in the water was 15.0 =/− 0.2 mg/L. If the oxygen level was below 15 mg/L, oxygen was bubbled through the water until the level was 15 mg/L. The water was standard APHA dilution water as described in the Standard Methods. The nutrient solution was prepared from 25 g peptone, 15 g beef extract, 4 g urea, 4 g glucose, and 3 g KH$_2$PO$_4$ dissolved into 1000 ml HPLC grade water. Over a five day period, the bacteria were given less nutrient solution and more QAC solution until the bacteria were not receiving any nutrient solution. On the first day the bacteria were fed 1 ml of nutrient solution and 10 mg of QAC. On the second day 1 ml of nutrient solution and 20 mg QAC was added to the culture. On the third day 0.5 ml nutrient solution was added to the culture along with 40 mg of QAC. On the fourth day 0.5 ml of nutrient solution and 80 mg QAC was added. On the fifth day 0.2 ml nutrient solution was added, along with 100 mg QAC and 1 ml diammoniun phosphate solution at a concentration of 24 g/L water. Fifty ml aliquots of HPLC water with a dissolved oxygen level of 15 mg O$_2$/L were added to the cultures each day after the first day. After the five day period 2 ml aliquots of the bacteria were immediately used in modified closed bottle testing.

Method

The procedure used for biodegradation evaluations was a variation of the Closed Bottle or Biochemical Oxygen Demand (BOD) method. The method used is as described in Method 507 of the Standard Methods for the Examination of Water and Wastewater (15th Ed., 1980) with the following exceptions: Classically the closed bottle test has been performed with activated sludge as the source of bacteria. Polyseed was selected to reduce the contribution of variable bacterial populations to experimental error. The bacterial composition was consistent within a lot of Polyseed and lot to lot variability was small. To eliminate any contribution to oxygen demand by organic materials in the water HPLC grade water was used.

Acclimation of bacteria is one of the key factors in determining the biodegradability of QAC's. The bacteria used in each closed bottle test were acclimated over a five day period as described above. When tests were repeated new acclimated bacteria were prepared.

Each round of testing included a water control, a seed correction, a glucose/glutamic acid control, and a series of QAC's. All of the samples were incubated in the dark at 20° C. Dissolved oxygen measurements were taken periodically, typically every 5, 10, 15, 20, 25 and 28 days. Tests were considered invalid if any one of the controls failed. Control failure included: (1) The dissolved oxygen level in the water control changed more than 0.2 mg/L after five days. (2) The seed correction sample showed a depletion outside the range 0.6-1.0 mg/L after five days. Calculations of % biodegradation were conducted using the ratios of biochemical oxygen depletion (mg sample) to calculated oxygen depletion (theoretical—based on empirical formula of primary molecule).

The results of the biodegradation tests and comparative softening evaluation are shown in Table III.

TABLE III

| Structure | Structure | % Degraded (20 day test) | Softening Ability |
|---|---|---|---|
| $[STC-N\underset{\diagdown\_\diagup}{\overset{CH_3}{\overset{|}{N}}}-CH_2CH_2OC(ST)]^+ \ Cl^-$ with C=O groups | XIV | 43 | Above average |
| $[(HT)_2-\overset{CH_3}{\underset{CH_3}{\overset{|}{N}}}]^+ \ Cl^-$ | X | 20 | Excellent |
| $[(ST)_2-\overset{CH_3}{\underset{CH_3}{\overset{|}{N}}}]^+ \ Cl^-$ | XV | 38 | Excellent |
| $HT-\underset{CH_3}{\overset{\underset{|}{(CH_2)_2-OH}}{N}}-(CH_2)_3NH\overset{O}{\overset{\|}{C}}(CH_2)_3O\overset{O}{\overset{\|}{C}}(ST)^+ \ MeSO_4^-$ | Ia | 43 | Above average |
| [di T imidazoline]$^{\oplus}$MeSO$_4^-$ | XII | 47 | Above average |
| $(T-\overset{O}{\overset{\|}{C}}-NHCH_2CH_2)_2-\overset{CH_3}{\underset{|}{N}}-N-CH_2CH_2OH^+ \ MeSO_4^-$ | XI | 48 | Average |

TABLE III-continued

| Structure | Structure | % Degraded (20 day test) | Softening Ability |
|---|---|---|---|
| 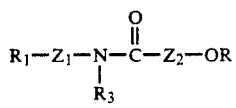 | XVI | 86 | Below average |

HT = hardened tallow alkyl (C$_{15}$–C$_{17}$)
T = unhardened tallow alkyl (C$_{15}$–C$_{17}$)
ST = stearyl It can be seen from Table III that the compound of this invention demonstrated better biodegradation when compared to competitive structures which show good softening performance.

The softener compositions of this invention may be effectively used in the dryer cycle of automatic laundry driers, as a rinse cycle softener system, or may be incorporated into a detergent system by procedures well known to the art. Additives which may advantageously used include optical brighteners, dyes, perfumes, enzymes, soil release agents or clays, etc.

An additional use for the compositions of this invention is in modification of clays. The use of quaternary salts of the clay modification is described in a paper by Tatum (Organo Clays. Special Publication Ray. Soc. Chems., 1987, p. 189. Chem. Abs. 106; 19861 SC). These modified clays find use in greases, inks, muds for oil well drilling and as thickeners for paints.

What is claimed is:

1. A compound of the formula:

$$R_1-Z_1-N(R_3)-\underset{\underset{O}{\|}}{C}-Z_2-OR$$

wherein
R is alkyl containing up to 22 carbon atoms, alkyl containing up to 22 carbon atoms and one or more ethylenic bonds, acyl containing 2 to 22 carbon atoms, or H;
R$_1$ is

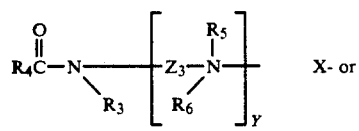   X⁻ or

   X⁻ or

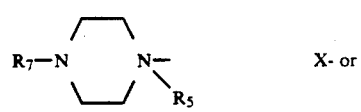   X⁻ or

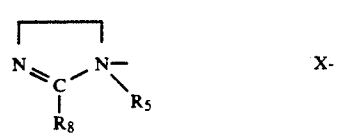   X⁻

$Z_1$, $Z_2$ and $Z_3$ are each alkylene containing 2–8 carbon atoms in the principal chain and a total of up to 15 carbon atoms;
Y is an integer from 1–3;
R$_3$ is methyl, ethyl or H;
R$_4$ and R$_8$ are each alkyl containing up to 22 carbon atoms, alkyl containing up to 22 carbon atoms and one or more ethylene bond, or —Z$_2$—OR;
R$_5$ is methyl, ethyl, hydroxymethyl, hydroxyethyl, or H;
R$_6$ is methyl, ethyl, hydroxymethyl, hydroxyethyl, or benzyl;
R$_7$ is $$RO-Z_2-\underset{\underset{O}{\|}}{C}-;\text{ and}$$

X— is a salt forming anion.

2. The compound according to claim 1 wherein R$_1$ is

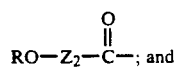

$Z_1$ is propylene; R$_3$ is H, $Z_3$ is alkylene containing 3–5 carbon atoms and R$_4$ is alkyl containing 12–22 carbon atoms.

3. The compound according to claim 2, wherein R$_5$ is methyl; R$_6$ is hydroxyethyl, and X is chloride, methylsulfate or methylcarbonate.

4. The compound according to claim 3, wherein Z$_2$ is propylene; R is acyl and X is chloride or methylsulfate.

5. The compound according to claim 4, wherein R is C$_{12}$–C$_{22}$ acyl.

6. A compound according to claim 1, wherein R$_1$ is

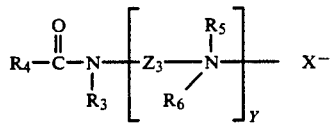

7. The compound according to claim 6, wherein R$_3$ is H; R$_1$ and Z$_3$ are ethylene and Y is 1.

8. The compound according to claim 6, wherein R$_4$ is —Z$_2$ — OR.

9. The compound according to claim 6, wherein R is acyl containing 12–22 carbon atoms and Z$_2$ is propylene.

10. The compound according to claim 1, wherein R$_1$ is

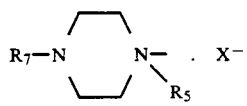

11. The compound according to claim 10, wherein $Z_1$ is ethylene and $R_3$ is H.

12. The compound according to claim 11, wherein $Z_2$ is propylene and R is acyl containing 12-22 carbon atoms.

13. The compound according to claim 12, wherein $R_7$ is

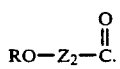

14. The compound according to claim 11, wherein $R_7$ is acyl containing 12-22 carbon atoms.

15. The compound according to claim 1, wherein $R_1$ is

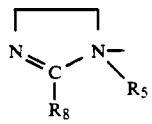

wherein $R_8$ is alkyl having 12-22 carbon atoms.

16. The compound according to claim 15, wherein $Z_1$ is ethylene and $R_3$ is H.

17. The compound according to claim 16 wherein R is acyl having 12-22 carbon atoms; $R_5$ is alkyl or hydroxyethyl and $Z_2$ is propylene.

18. A composition for softening clothes in an automatic dryer comprising a compound according to claim 1.

19. A clothes softening composition for use in the rinse cycle comprising a compound according to claim 1, dispersed in an aqueous carrier and optionally containing colorants, perfumes, anti-soil redeposition agents or optical brighteners.

20. An organophilic clay composition comprising a compound according to claim 1.

21. A compound of the formula:

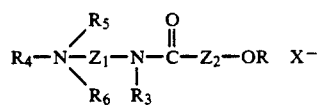

wherein
R is alkyl containing up to 22 carbon atoms, alkyl containing up to 22 carbon atoms and one or more ethylenic bonds, acyl containing 2 to 22 carbon atoms, or H;
$Z_1$ and $Z_2$ are each alkylene containing 2-8 carbon atoms in the principal chain and a total of up to 15 carbon atoms;
$R_3$ is methyl, ethyl or H;
$R_4$ is alkyl containing up to 22 carbon atoms, alkyl containing up to 22 carbon atoms and one or more ethyleneic bonds or —$Z_2$—OR;
$R_5$ is methyl, ethyl, hydroxymethyl, hydroxyethyl or H;
$R_6$ is methyl, ethyl, hydroxymethyl, hydroxyethyl, or benzyl;
and X— is a salt forming anion.

22. A compound of the formula:

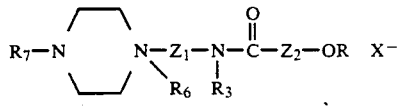

wherein
R is alkyl containing up to 22 carbon atoms, alkyl containing up to 22 carbon atoms and one or more ethylenic bonds, acyl containing 2 to 22 carbon atoms, or H;
$Z_1$ and $Z_2$ are each alkylene containing 2-8 carbon atoms in the principal chain and a total of up to 15 carbon atoms;
$R_3$ is methyl, ethyl or H;
$R_5$ is methyl, ethyl, hydroxymethyl, hydroxyethyl, or H;
$R_7$ is

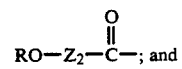

X— is a salt forming anion.

23. A compound of the formula:

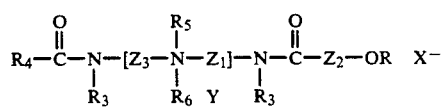

wherein
R is alkyl containing up to 22 carbon atoms, alkyl containing up to 22 carbon atoms and one or more ethylenic bonds, acyl containing 2 to 22 carbons atoms, or H;
$Z_1$, $Z_2$ and $Z_3$ are each alkylene containing 2-8 carbon atoms in the principal chain and a total of up to 15 carbon atoms;
$R_3$ is methyl, ethyl or H;
$R_4$ is alkyl containing up to 22 carbon atoms, or —$Z_2$—OR;
$R_5$ is methyl, ethyl, hydroxymethyl, hydroxyethyl, or H;
$R_6$ is methyl, ethyl, hydroxymethyl, hydroxyethyl, or benzyl;
X— is a salt forming anion; and
Y is an integer from 1-3.

24. A compound of the formula:

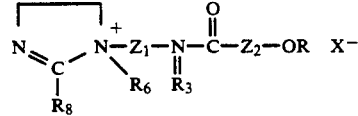

wherein
R is alkyl containing up to 22 carbon atoms, alkyl containing up to 22 carbon atoms and one or more ethylenic bonds, acyl containing 2 to 22 carbon atoms, or H;
$R_3$ is methyl, ethyl or H;
$R_4$ and $R_8$ are each alkyl containing 2 to 22 carbon atoms, alkyl containing 2 to 22 carbon atoms and one or more ethylenic bonds or —$Z_2$—OR;
$R_6$ is methyl, ethyl, hydroxymethyl, hydroxyethyl or H;
$Z_1$ and $Z_2$ are each alkylene containing 2-8 carbon atoms in the principal chain and a total of up to 15 carbon atoms; and
X— is a salt-forming anion.

* * * * *